(12) United States Patent
Fournie et al.

(10) Patent No.: US 7,080,672 B2
(45) Date of Patent: Jul. 25, 2006

(54) SLIDING SEAL ADAPTER FOR A FEEDING SYSTEM

(75) Inventors: Glenn G. Fournie, Smithton, IL (US); Kevin C. Meier, Affton, MO (US)

(73) Assignee: Sherwood Services AG, Schaffhausen (CH)

( * ) Notice: Subject to any disclaimer, the term of this patent is extended or adjusted under 35 U.S.C. 154(b) by 289 days.

(21) Appl. No.: 10/852,428

(22) PCT Filed: Aug. 22, 2002

(86) PCT No.: PCT/US02/26666

§ 371 (c)(1),
(2), (4) Date: May 24, 2004

(87) PCT Pub. No.: WO2004/017852

PCT Pub. Date: Mar. 4, 2004

(65) Prior Publication Data

US 2004/0211484 A1 Oct. 28, 2004

(51) Int. Cl.
*B65B 1/04* (2006.01)

(52) U.S. Cl. .................. 141/383; 141/2; 141/319; 141/329; 141/364

(58) Field of Classification Search .......... 141/1, 141/2, 18, 319, 329, 330, 346, 363–366, 141/383–386
See application file for complete search history.

(56) References Cited

U.S. PATENT DOCUMENTS

| | | | |
|---|---|---|---|
| 3,931,818 A | 1/1976 | Goldowsky | |
| 4,187,846 A | 2/1980 | Carminucci et al. | |
| 4,508,367 A | 4/1985 | Oreopoulos et al. | |
| 4,534,758 A | 8/1985 | Akers et al. | |
| 4,567,999 A | 2/1986 | Hjertman et al. | |
| 4,576,211 A * | 3/1986 | Valentini et al. | 141/329 |
| 4,607,868 A | 8/1986 | Harvey et al. | |
| 4,888,008 A | 12/1989 | D'Alo et al. | |
| 5,041,105 A | 8/1991 | D'Alo et al. | |
| 5,053,015 A | 10/1991 | Gross | |
| 5,088,984 A | 2/1992 | Fields | |
| 5,113,571 A | 5/1992 | Manska | |
| 5,209,740 A | 5/1993 | Bryant et al. | |
| 5,215,538 A | 6/1993 | Larkin | |
| 5,226,898 A | 7/1993 | Gross | |
| 5,303,751 A | 4/1994 | Slater et al. | |
| 5,380,306 A | 1/1995 | Brinon | |
| 5,456,676 A | 10/1995 | Nelson et al. | |
| 5,492,147 A * | 2/1996 | Challender et al. | 137/614.05 |
| 5,607,392 A | 3/1997 | Kanner | |
| 5,624,414 A | 4/1997 | Boettger | |
| 5,782,808 A | 7/1998 | Folden | |
| 5,830,195 A | 11/1998 | Peters et al. | |
| 5,976,115 A | 11/1999 | Parris et al. | |
| 6,183,465 B1 | 2/2001 | Meier et al. | |

FOREIGN PATENT DOCUMENTS

WO   WO 96/26701   9/1996

* cited by examiner

*Primary Examiner*—Timothy L. Maust

(57) ABSTRACT

An adapter (10) utilized to interconnect a fluid container (88) and an administration feeding set (90) having a hollow retractable spike (52) and a sliding shaft seal (18) for maintaining a fluid-tight seal around spike (52). The sliding shaft seal (18) includes a conduit (77) which sealingly engages around the retractable spike (52) in fluid tight engagement when adapter (10) is biased by a spring (19) between an engaged position and a disengaged position.

16 Claims, 12 Drawing Sheets

SLIDING SEAL ADAPTER FOR A FEEDING SYSTEM

RELATED APPLICATIONS

This application is a 371 National Phase Application for International Application PCT/US02/26666, filed Aug. 22, 2002.

BACKGROUND OF THE INVENTION

1. Field of the Invention

The present invention generally relates to an adapter for interconnecting a fluid container with an administration feeding set, and more particularly to an adapter having a retractable spike for use with a feeding system.

2. Prior Art

Feeding systems are frequently used to provide nutrition through either enteral or parenteral access to a patient unable to take nutrition orally. As used herein, the term nutrition shall be interpreted to include nutrition, medication and hydration. These feeding systems typically comprise an administration feeding set attached to a source of nutrition at one end and some kind of tube arrangement at the other end for providing nutrition immediately to a patient. In enteral feeding, the nutrition is typically administered to the patient by accessing a digestive organ through use of a nasogastric or gastrostomy tube which terminates in the stomach, or a nasojejunal or jejunostomy tube which terminates in the jejunum. In contrast, parenteral feeding typically includes feeding nutrition by injection into a vein. Such feeding systems also include fluid containers which hold nutritional fluid in liquid form and typically include an opening sealed with a flexible membrane to seal and isolate the contents from environmental contaminants.

Often fluid containers of the above-mentioned character are connected to the administration feeding set by an adapter. One such adapter typical of the prior art is disclosed in U.S. Pat. No. 4,567,999 to Hjertman et al. entitled "Self-adhesive Connecting Device." Hjertman discloses an adapter for providing a sealed liquid connection with the orifice of a fluid container formed from a flexible sheet material. The adapter includes a hollow chamber with an outside surface adapted to be adhered to the container wall and a sharp point that is encased therein which is operative to penetrate the wall of the container. A pressure sensitive adhesive is provided on the outer peripheral surface of the Hjertman adapter that is intended to attach the adapter to the container wall such that the hollow chamber is sealed from outside contaminates.

Although the device of Hjertman et al. effectively provides a sealed liquid connection with a container, such devices also have several inherent drawbacks. Because the device to Hjertman entirely encloses the sharp point within the chamber, the user of these devices would need to apply a sufficiently strong exterior force to the chamber in order to actuate the device. However, directly exerting an exterior force upon the chamber to actuate the device increases the possibility of rupturing the chamber and resulting in mechanical failure of the device. Moreover, inadvertent impacts upon the chamber during transportation and storage are also likely to result in premature rupturing of the chamber. Finally, properly adhered to the container, such devices cannot be easily reused with other fluid containers.

Other connection devices have been suggested to further advance the art. For instance, U.S. Pat. No. 5,041,105 to D'Alo et al. entitled "Vented Spike Connection Component," which is assigned to the assignee of the present invention, discloses a connection component suitable for use with a feeding system which includes a fluid container having a cap with an orifice and external threading disposed about the cap. A foil, or other similar frangible material, seals off the orifice of the container from fluid flow and outside contaminants. The connection component includes internal threading that mates with the external threading of the cap and a projecting spike which is adapted to penetrate the foil seal and establish fluid flow as the connection component is attached to the fluid container and actuated.

Although the D'Alo et al. device substantially advances the art, such connection components could still be further improved upon. The device to D'Alo et al. relies solely on frictional engagement between the threaded portion of the housing body and the threaded portion of the cap to create and maintain a fluid-tight seal. The device to D'Alo et al. also operates to simultaneously pierce the container when the user connects the connection component, and thus the operator must interconnect the device at the precise moment when it is desired to establish fluid flow. In other words, the operator cannot attach the D'Alo et al. device to the pre-filled container without instantaneously piercing the foil seal and establishing fluid flow which may be undesirable. Accordingly, the operator must delay attaching the device to the container until needed, or the operator must attach the device to the fluid container and immediately establish fluid flow when the foil seal is pierced by the device connection.

Therefore, one skilled in the art can best appreciate that several advances would still be desirable. It would be desirable to have a connection device that may be properly secured to the container, while allowing the operator to delay piercing the fluid container and establish fluid flow when needed. It would also be desirable to have a connection device which provides a leak-free seal at all times between the fluid container, the connection device, and the administration feeding set. It would be further desirable to have a spike of the connection device which is shielded from touch contamination by the user.

OBJECTS AND SUMMARY OF THE INVENTION

A primary object of the present invention is to provide an adapter which is capable of establishing fluid flow communication between a fluid container and an administration feeding set while maintaining a fluid-tight seal therebetween at all times.

A further object of the present invention is to provide an adapter having a sliding shaft seal that maintains a fluid-tight seal around the axial spike during operation of the adapter.

Another object of the present invention is to provide a connection device that allows the container to be sealingly connected to the administration feeding set without simultaneously piercing the flexible membrane of the fluid container.

Another further object of the present invention is to provide an adapter having a retractable touch free spike that is shielded from touch contamination by the user.

In brief summary, the present invention overcomes and substantially alleviates the deficiencies in the prior art by providing an adapter that includes a sliding shaft seal which provides a leak-free connection site and shields the shaft from contamination. The adapter operates as a connector between a fluid container and an administration feeding set with the fluid container having a cap that has an orifice and an external threading disposed about the cap. A foil, or other frangible membrane, seals off the orifice of the container from fluid flow prior to use. The administration feeding set includes hollow flexible tubing which interconnects a tube arrangement attached to a patient to the fluid container via the adapter of the present invention.

The adapter comprises a body member connected between a spike member and a locking collar. The body member includes a body portion having a generally cylindrical shape and an annular ring formed thereon with a plurality of protrusions which are longitudinally formed along the body member. A pair of leg portions axially extends from the body portion with retention tabs formed at the free end thereof for engaging the body member to the spike member. The adapter further comprises a sliding shaft seal positioned within the body member for providing a leak-free seal within the adapter during operation.

The spike member is coupled to the body member and includes a spike body which is generally frusto-conical in shape with an opposed pair of slots formed longitudinally along the spike body which are sized and shaped to slidably receive corresponding protrusions formed along the body portion. An axial spike to penetrate the seal of the fluid container outwardly extends from the spike body and includes a longitudinal slot formed therealong which terminates at an angularly skewed pointed end. Two generally opposed openings are formed through the spike body and are sized and shaped to receive and securely retain a respective leg portion of the body member thereto. As a result, the spike member is slidably coupled with the body member. The spike member also includes a tube adapter at its proximal end which axially extends therefrom and is adapted to attach the adapter of the present invention to the administration feeding set. A coiled spring is provided to apply a spring force against the spike member for actuating and biasing the adapter during operation thereof.

The locking collar is coupled to the body member and has a hollow cylindrical shape forming a channel with opposed openings. An annular groove is formed adjacent one of the openings and is sized and shaped to be engaged by the annular ring formed around the body member such that the locking collar is engaged to the body member, but rotates freely thereabout. The locking collar also includes an internal threaded portion defined about the channel proximate the other opposed opening for mating engagement with the external threaded portion of the fluid container when the adapter is attached thereto.

One unique aspect of the present invention is that it includes a sliding shaft seal disposed at least partially within the body member and around the axial spike. The sliding shaft seal includes a hollow, flexible body defining a conduit formed between opposed proximal and distal ends which define respective openings. The sliding shaft seal further includes a sealing flange formed proximate the proximal opening, while a locking flange is formed proximate the distal opening. In assembly, the sliding shaft seal is disposed within the body member such that the shaft of the spike is sealingly surrounded by the conduit of the sliding shaft seal. The spring is co-axially aligned with and engaged to the sliding shaft seal for applying a spring force against the spike body during operation.

In operation, the operator of the present invention may easily and securely connect the adapter between the fluid container and the administration feeding set by first threading the threaded portion of the locking collar onto the threaded portion of the cap while the spike is isolated within the locking collar from inadvertent contact with outside contaminants which may result in contamination of the spike. It will be appreciated that, although the adapter is secured to the container, the spike does not simultaneously pierce and breach the foil that seals off the orifice of the fluid container until actuated by the user. Once the locking collar is properly secured, the administration feeding set is connected between the patient's tube arrangement and the adapter, while the spike member is maintained in the disengaged position. The operator will then grasp the spike body between the thumb and forefinger and move the spike member axially forward relative to the body member and against the spring force applied by the spring so that the spike extends forward through the locking collar and is driven through the foil of the fluid container, thereby establishing fluid flow through the spike. After the foil has been breached and fluid flow established, the operator will then release the spike member which will then be biased back within the locking collar by the spring force applied by the spring. During operation of the adapter, the sliding shaft seal maintains a fluid tight seal about the axial spike as the spike is moved longitudinally during actuation. When fluid flow communication is established with the fluid container the sliding shaft seal continues to maintain a fluid tight seal around the spike, while preventing the user to touch and contaminate the spike during operation.

These and other objects of the present invention are realized in the preferred embodiment of the present invention, described by way of example and not by way of limitation, which provides for an adapter having a retractable spike including a sliding shaft seal for establishing leak-free fluid flow communication along the spike.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
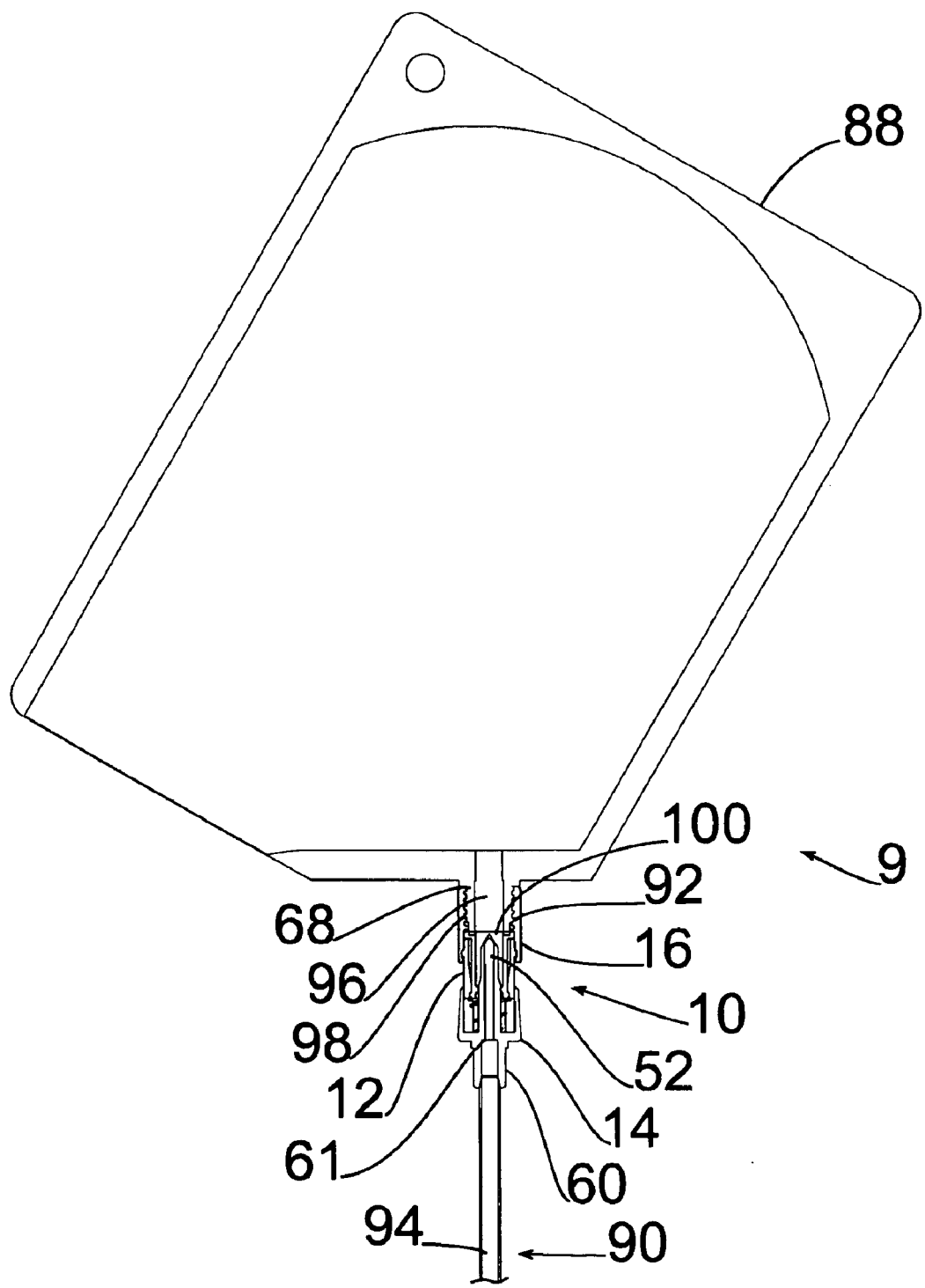
FIG. 1 is a cross-sectional view of a preferred embodiment of the adapter connected between a fluid container and an administration feeding set according to the present invention.
Figure 2:
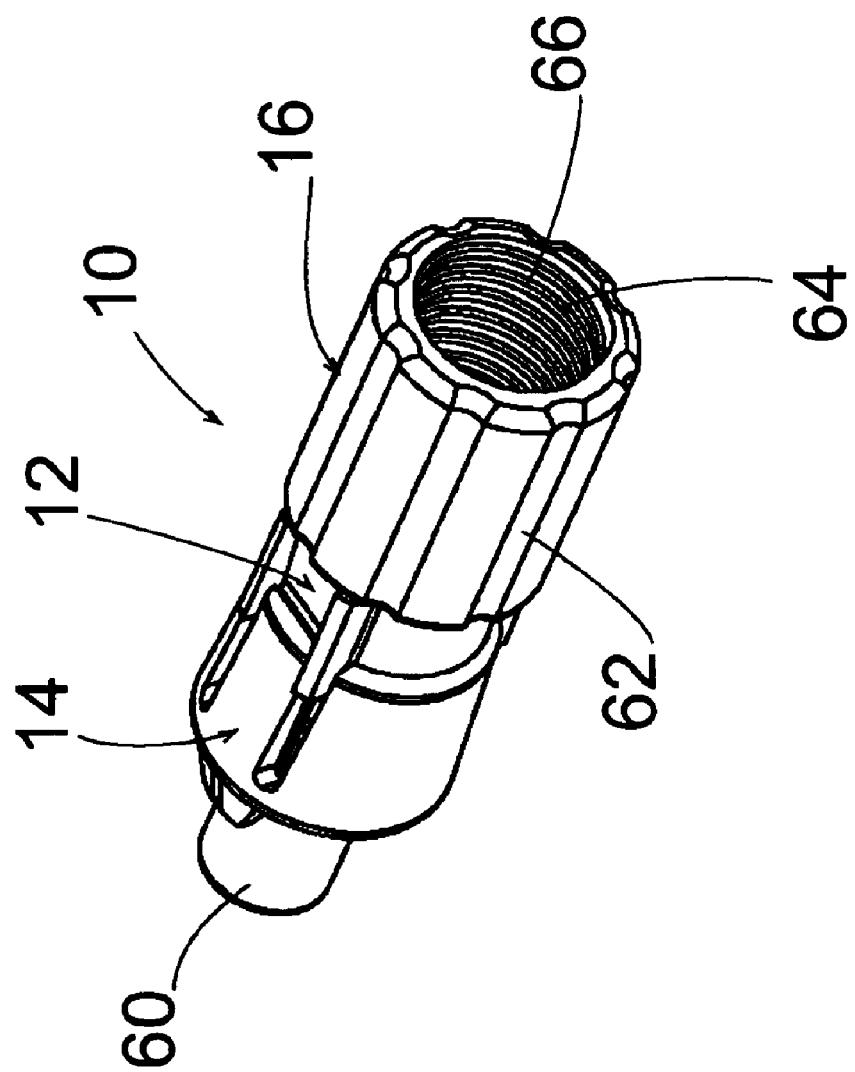
FIG. 2 is a perspective view of a preferred embodiment of the adapter according to the present invention.

Referring to the drawings, the preferred embodiment of the adapter for a feeding system 9 of the present invention is illustrated and generally indicated as 10 in FIG. 1. As shown, adapter 10 operates as a connector between a fluid container 88 and an administration feeding set 90 with the fluid container 88 including a cap 92 that has an orifice 96 and threading 98 formed about the cap 92. A foil 100, or other frangible membrane, seals off the orifice 96 of container 88 from fluid flow. The administration feeding set 90 includes tubing 94 which interconnects a tube arrangement (not shown) which is connected to the fluid container 88 via the adapter 10 of the present invention. Referring to FIG. 2, the adapter 10 comprises a body member 12 slidably connected to a biased spike member 14 and rotatably connected to a locking collar 16. In addition, as shown in FIG. 3, adapter 10 further includes a sliding shaft seal 18 disposed within the body member 12 for providing a fluid tight seal between the adapter 10 and fluid container 88.

As further shown, body member 12 comprises a hollow body portion 20 having opposed openings 25, 27 which form a channel 31 therebetween with a pair of laterally opposed leg portions 26 which extend axially proximate the opening 27. Preferably, body member 12 has a pair of leg portions 26, although in the alternative, one skilled in the art can best appreciate that any suitable number of leg portions 26 may be utilized without departing from the teachings of the present invention. Each leg portion 26 includes a tab 22 formed at the free end thereof. Preferably, tabs 22 are bifurcated along the free end thereof.

The body member 12 further includes an interior annular ridge 23 formed adjacent opening 27 and two pairs of opposed protrusions 28 longitudinally aligned and extending along the body portion 20. Formed between each pair of protrusions 28 is a beveled portion 30 defining a ledge 32. Further, body member 12 includes an exterior annular flange 34 formed proximate opening 25. Alternatively, it should be appreciated that any suitable number of protrusions 28 may be utilized.

Figure 3:
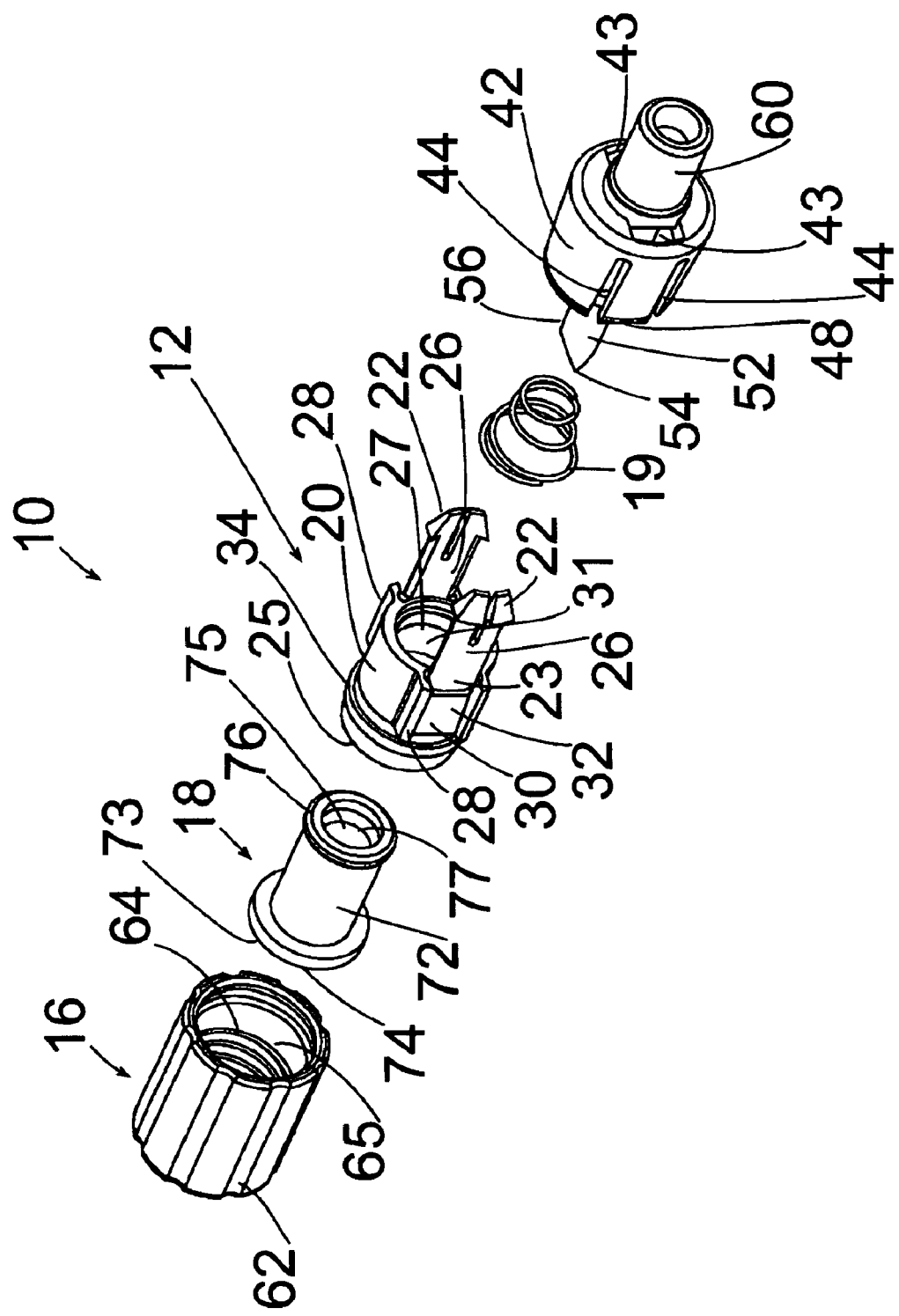
FIG. 3 is an exploded perspective view of the preferred embodiment of the adapter according to the present invention.
Figure 4A:
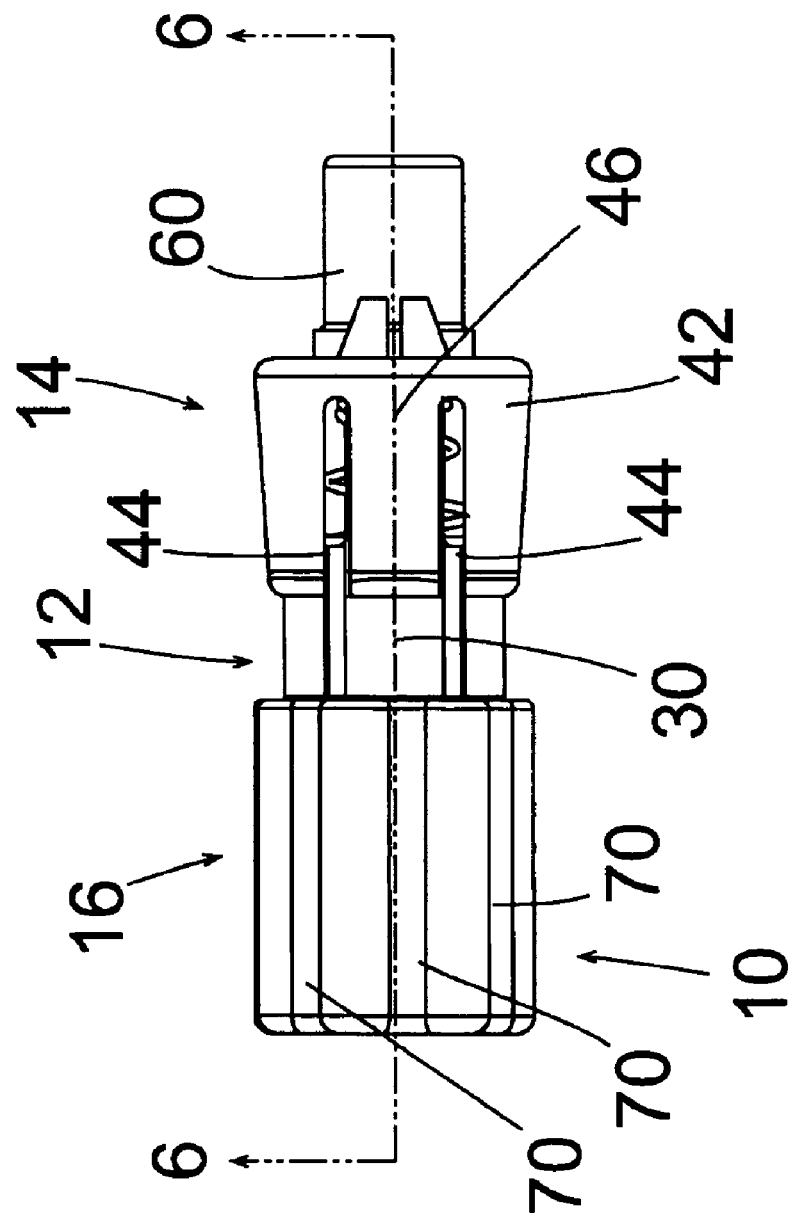
FIG. 4a is a side elevational view of the preferred embodiment of the adapter in an unactuated position according to the present invention.
Figure 4B:
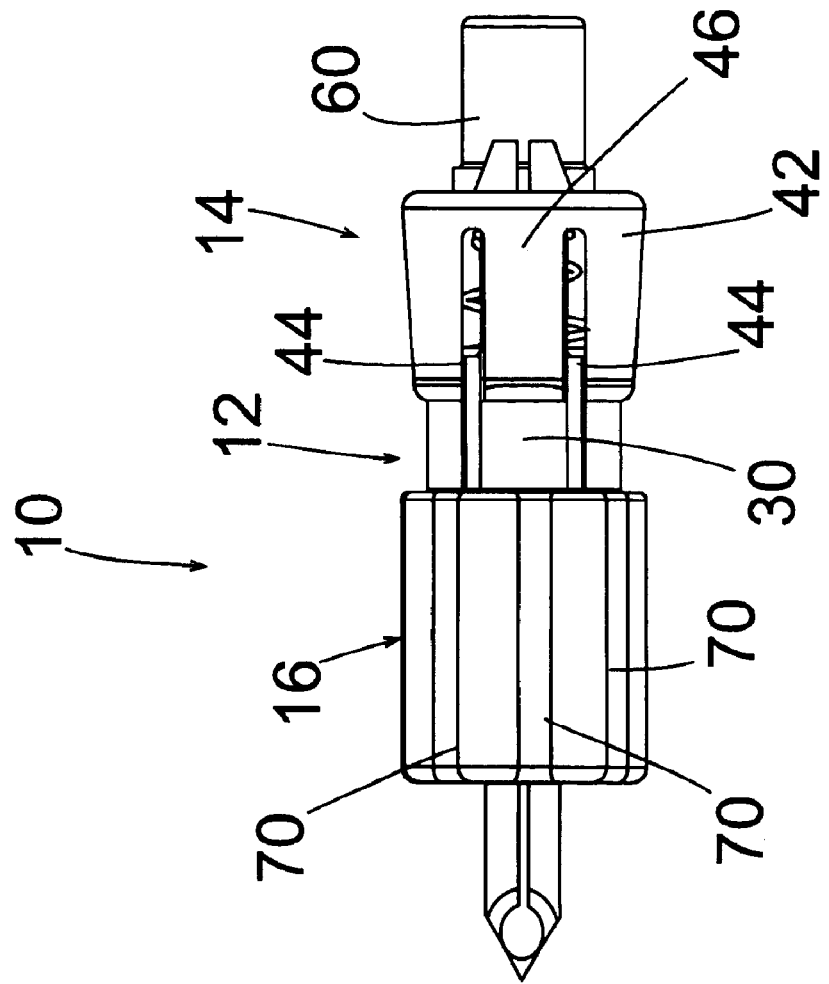
FIG. 4b is a side elevational view of an alternative embodiment of the adapter in an unactuated position according to the present invention.

As seen in FIGS. 3, 4a, and 4b, spike member 14 of adapter 10 comprises a spike body 42 defining two opposed pairs of longitudinal slots 44 which are adapted to correspond to the two opposed pairs of protrusions 28 formed on body member 12. Each slot 44 is sized and shaped to slidably receive a corresponding protrusion 28 when the spike member 14 is in the actuated position, as shall be discussed in greater detail below. In addition, spike member 14 further includes two axial openings 43, as particularly shown in FIG. 3, which are sized and shaped to receive and retain a corresponding tab 22 of each leg portion 26 when inserted therethrough. Alternatively, one skilled in the art can appreciate that any number of slots 44 and openings 43 may be utilized to interconnect the body member 12 to spike member 14 without departing from the teachings of the present invention.

Figure 6:
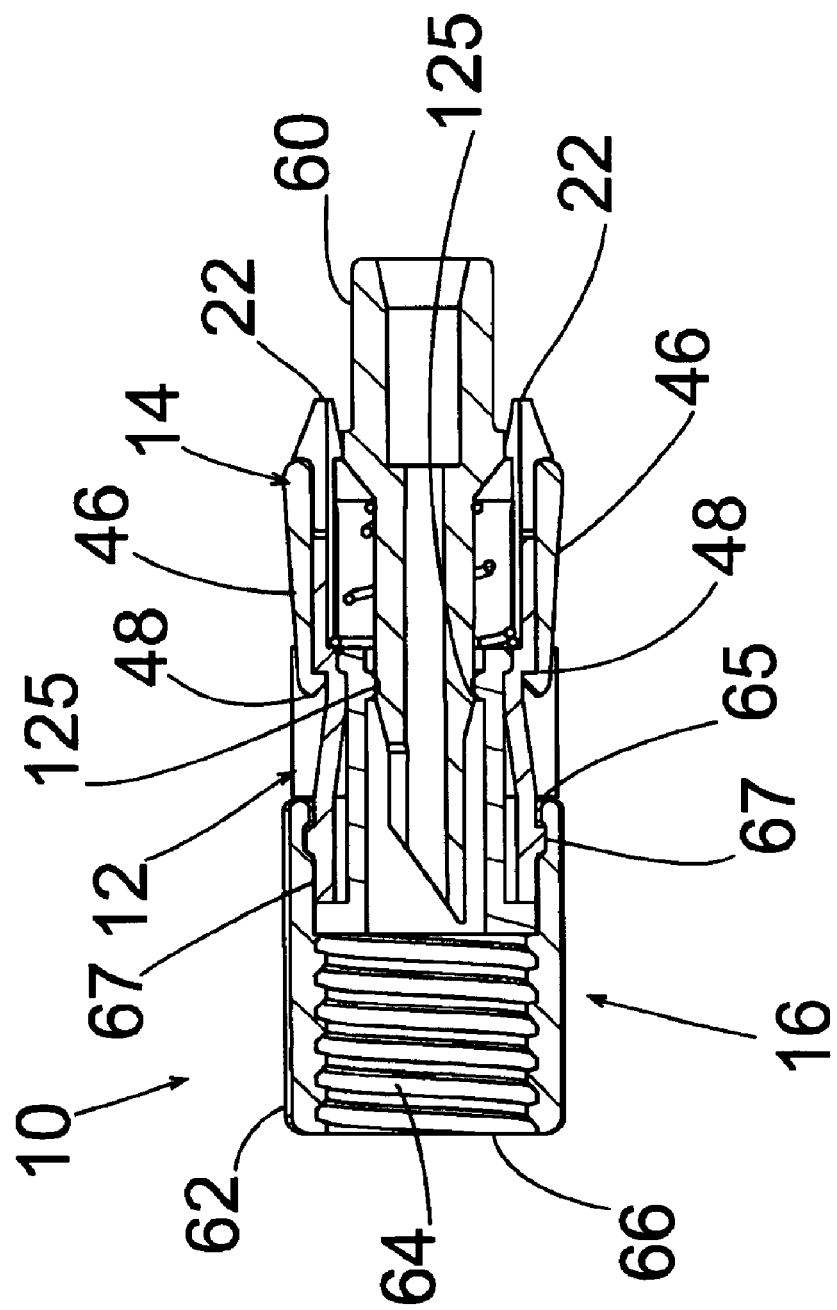
FIG. 6 is a cross-sectional view of the preferred embodiment of the adapter shown along line 6—6 of FIG. 4a according to the present invention.

With reference to FIGS. 4a, 4b, and 6, each pair of slots 44 defines a retention section 46 which includes a retention edge 48 formed at a distal or free end of each section 46. Each retention section 46 is positioned between a respective corresponding pair of protrusions 28 and is adapted to slide between each pair of protrusions 28 while traveling along the corresponding beveled portion 30 formed along the body member 12. During the aforementioned sliding action, the retention section 46 is prevented from separating from body member 12 due to the engagement between retention edge 48 of spike member 14 and the ledge 32 formed along body member 12 as well as the relative action of tab 22 with spike body 42, as shall be described in greater detail later.

Figure 7:
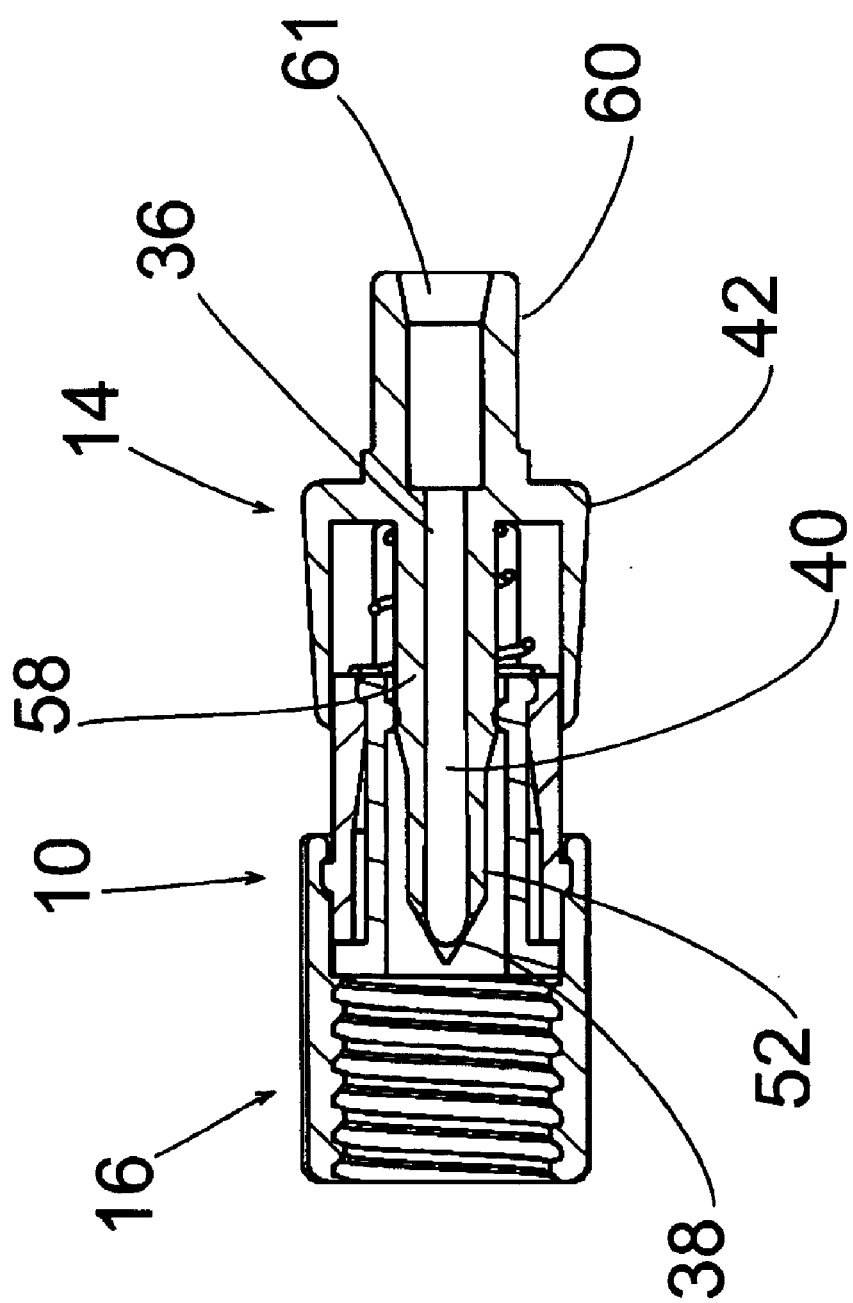
FIG. 7 is a cross-sectional of the preferred embodiment of the adapter shown along line 7—7 of FIG. 5 according to the present invention.

As best appreciated in FIG. 7, spike member 14 further includes a hollow axial spike 52 outwardly extending from the spike body 42 defining opposed ends 36, 38 which form a channel 40 therebetween. With particular reference to FIG. 3, spike 52 includes a distal longitudinal slot 56 formed along a portion of spike 52 and that terminates at an angularly skewed end 54 for receiving fluid flow therethrough. Referring back to FIG. 7, circumferentially disposed about the spike 52 is a shoulder portion 58 which assists in forming a seal between the spike member 14 and sliding shaft seal 18. Spike body 42 further includes a proximal tube adapter 60 formed opposite spike 52 which is bonded to administration feeding set 90. Spike 52 has an opening 61 in communication with slot 52 and co-axially aligned with spike 52 proximate end 36 which is sized and shaped to be bonded to administration feeding set 90, as illustrated in FIG. 1. As further shown, a spring 19 having an opening 120 is provided for applying a spring force against spike member 14 during operation of adapter 10. Preferably, spike 52 is disposed entirely within the adapter 10 as illustrated in FIG. 4a. In an alternative embodiment shown in FIG. 4b, spike 52 extends beyond the collar 16 when adapter 10 is fully assembled.

Referring to FIGS. 2, 3 and 6, adapter 10 of the present invention also includes locking collar 16 comprising a body portion 62 with opposed openings 65, 66 forming a channel 64 therebetween. Channel 64 includes an annular groove 67 formed proximate opening 65 and a threaded portion 68 formed proximate opening 66. As seen in the preferred embodiment shown in FIG. 4a, longitudinal grooves 70 are formed along the body portion 62 of the locking collar 16 to enhance the ability of the user to grasp the locking collar 16. However, one skilled in the art can best appreciate that a variety of other connective arrangements may be utilized without departing from the teachings of the present invention.

Figure 10:
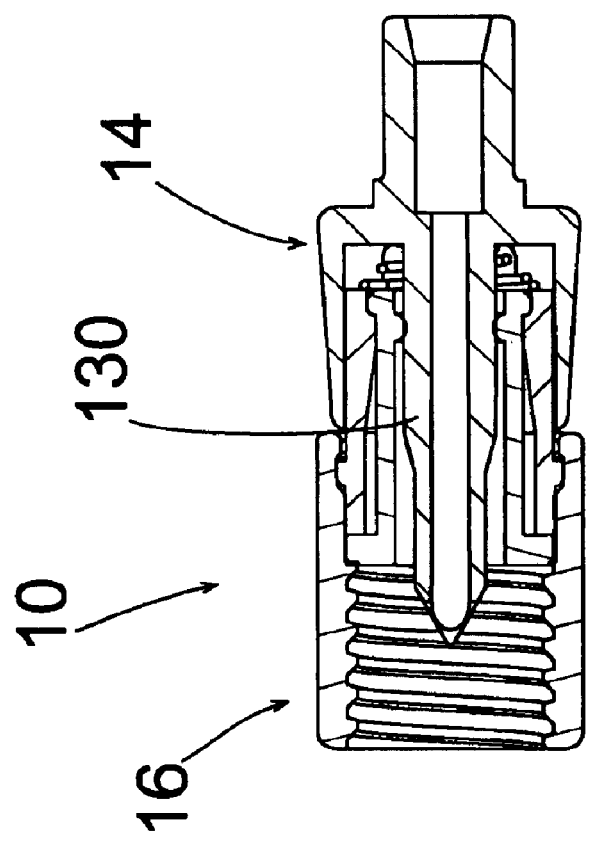
FIG. 10 is a cross-sectional view of the preferred embodiment of the adapter shown along line 10—10 of FIG. 8 according to the present invention.

As illustrated in FIG. 3, one unique aspect of adapter 10 is that it includes sliding shaft seal 18 which forms and maintains a fluid-tight seal around axial spike 52 during operation of adapter 10. With reference to FIGS. 3 and 10, sliding shaft seal 18 comprises a body portion 72 which includes a pair of opposed proximal and distal openings 73, 75 with a conduit 77 formed therebetween. Conduit 77 is sized and shaped to provide a sealing engagement with spike 52 along a small percentage of the length of conduit 77 at any one time. As illustrated in FIG. 6, an O-ring portion 125 is preferably molded to conduit 77 at a strategic location therealong for providing the sliding seal engagement with spike 52. This sealing engagement by the sliding shaft seal 18 is provided about spike 52 whether adapter (10) is actuated, i.e. during operation, or unactuated, i.e. when the spike 52 is in a free state with the spike 52 retracted. A lubricant can be applied along the spike 52 and/or conduit 77 for lowering the coefficient of friction between sliding shaft seal 18 and spike 52. Sliding shaft seal 18 further comprises a sealing flange 74 disposed proximate proximal opening 73 and circumferentially disposed about the body portion 72, while a locking flange 16 is formed proximate distal opening 75.

Figure 5:
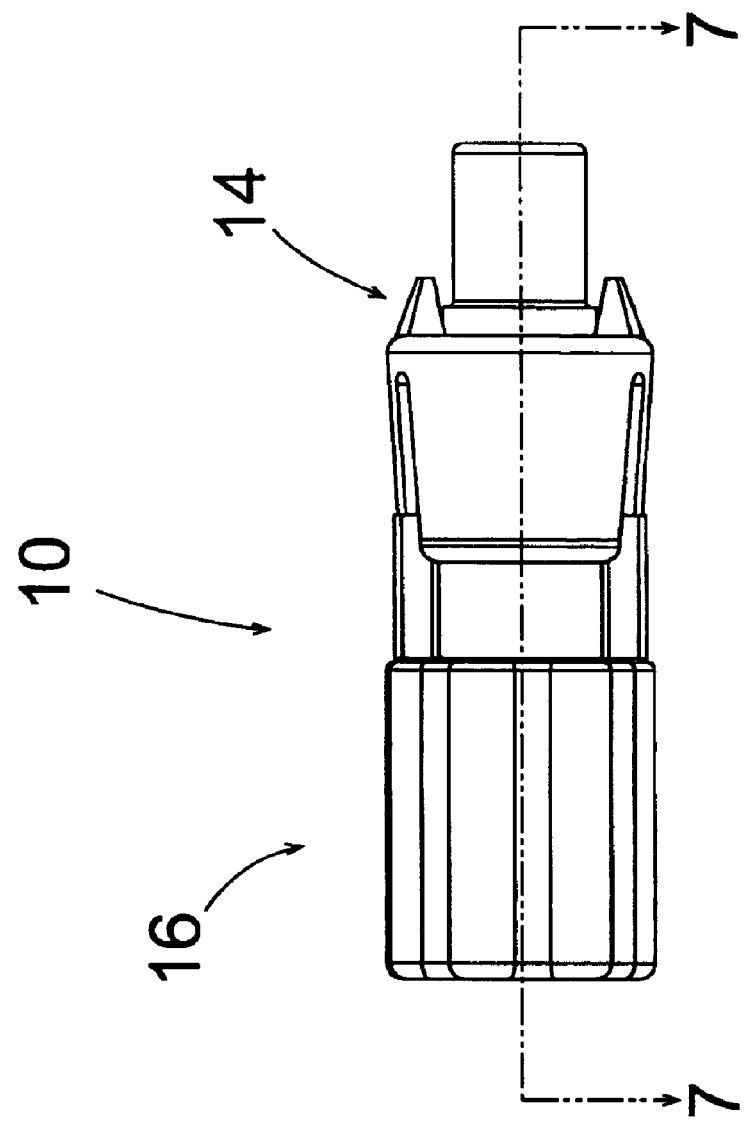
FIG. 5 is a top plan view of the preferred embodiment of the adapter in an unactuated position according to the present invention.
Figure 11:
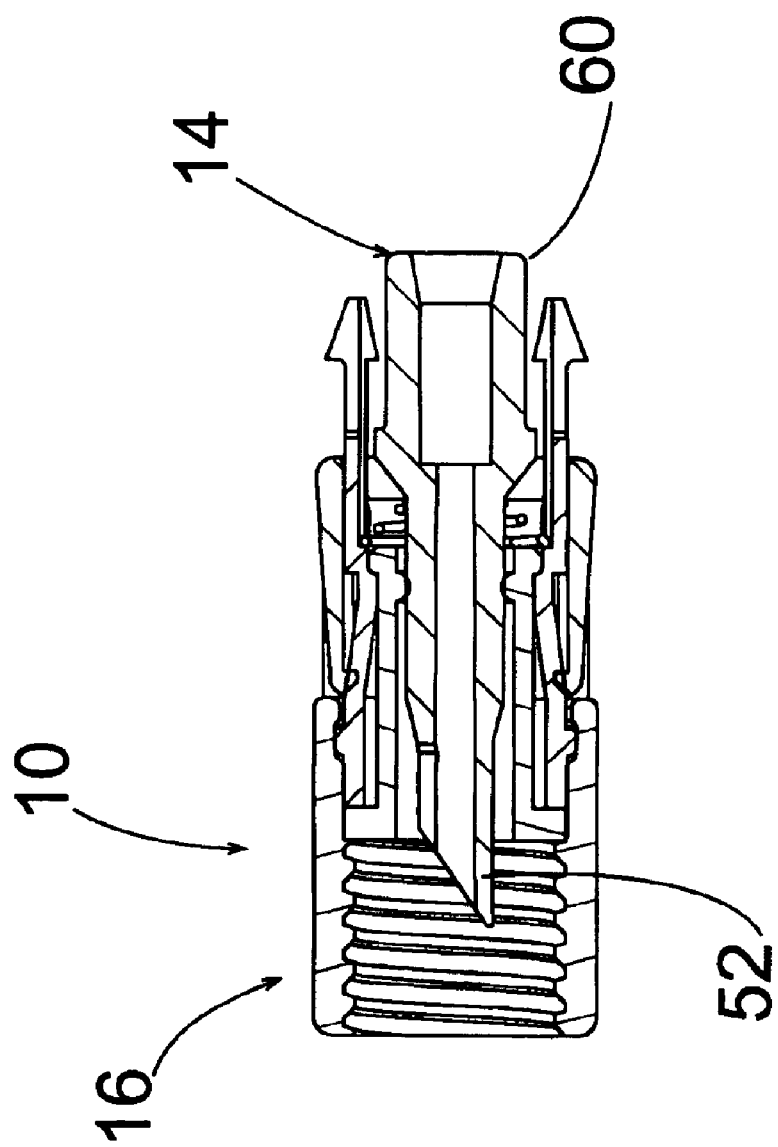
FIG. 11 is a cross-sectional view of the preferred embodiment of the adapter shown along line 11—11 of FIG. 9 according to the present invention.

With particular reference to FIG. 3, adapter 10 is assembled during manufacturing by first inserting the sliding shaft seal 18 within body member 12 by placing distal end 75 of shaft seal 18 through opening 25. Sliding shaft seal 18 is then aligned within channel 31 such that the locking flange 76 crowns the ridge 23, while the sealing flange 74 abuts the opening 25 of body member 12 so that sliding shaft seal 18 is properly secured within body portion 20 of body member 12. Next, the locking collar 16 is then engaged about the body member 12 so that annular flange 34 of body member 12 is engagingly received within the annular groove 66 of locking collar 16. Spring 19 is placed between leg portions 26 of body member 12 such that distal opening 75 of sliding shaft seal 18 is properly aligned with opening 120 of Spring 19. The spike 52 of spike body 42 is then inserted through the respective openings 120, 75 of spring 19 and sliding shaft seal 18 respectively such that tabs 22 on each leg portion 26 are inserted through the longitudinal slots 44 of spike body 42. Spike member 14 is then connected to body member 12 and aligned so that each protrusion 28 is slidably received within each corresponding slot 44 of spike body 42. Spike member 14 is then axially depressed onto body member 12 until tabs 22 are passed through the corresponding openings 43 and retention edge 48 is disposed adjacent the beveled portion 30. Once so assembled, spike member 14 may be biased between two positions by the user: an actuated position, wherein spike member 14 abuts locking collar 16, as illustrated in FIGS. 10 and 11, and an unactuated position, wherein spike member 14 abuts tabs 22 of the body member 12, as seen in FIGS. 4a and 5.

Figure 8:
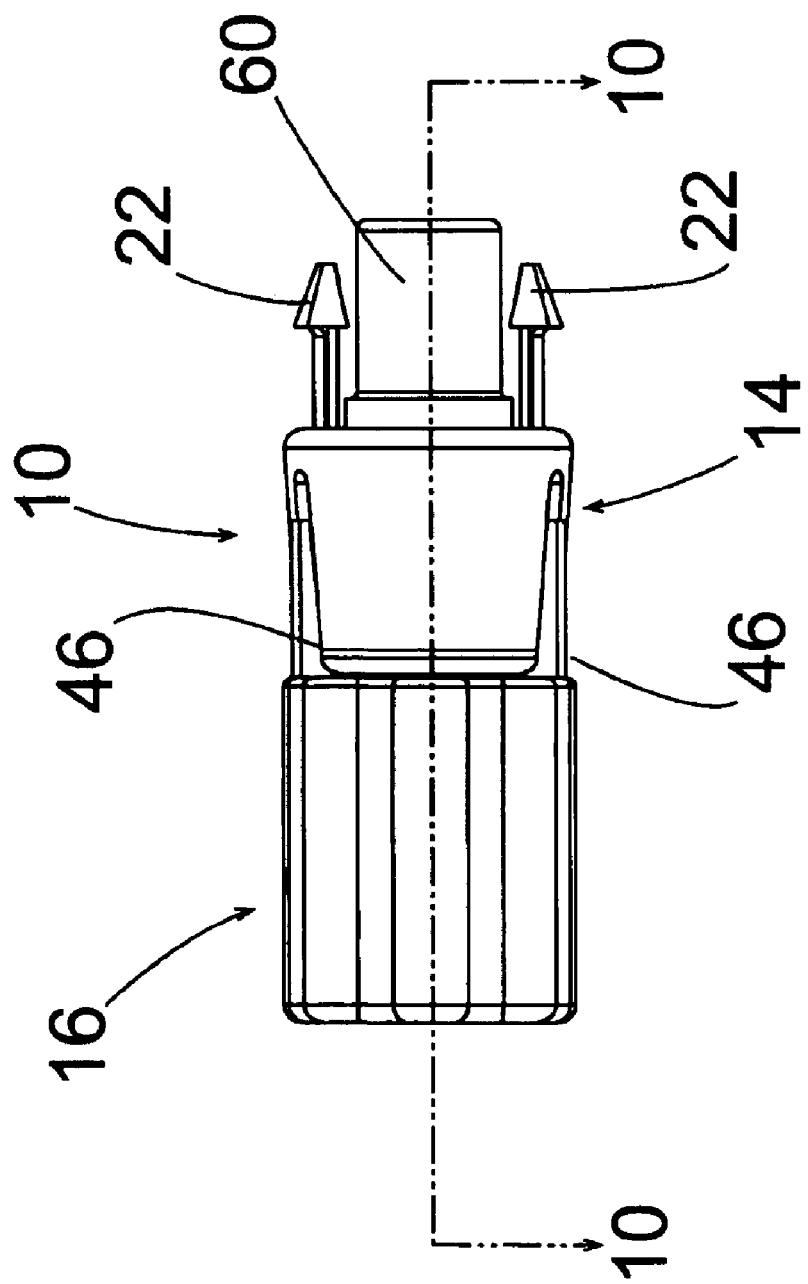
FIG. 8 is a top plan view of the preferred embodiment of the adapter in an actuated position according to the present invention.
Figure 9:
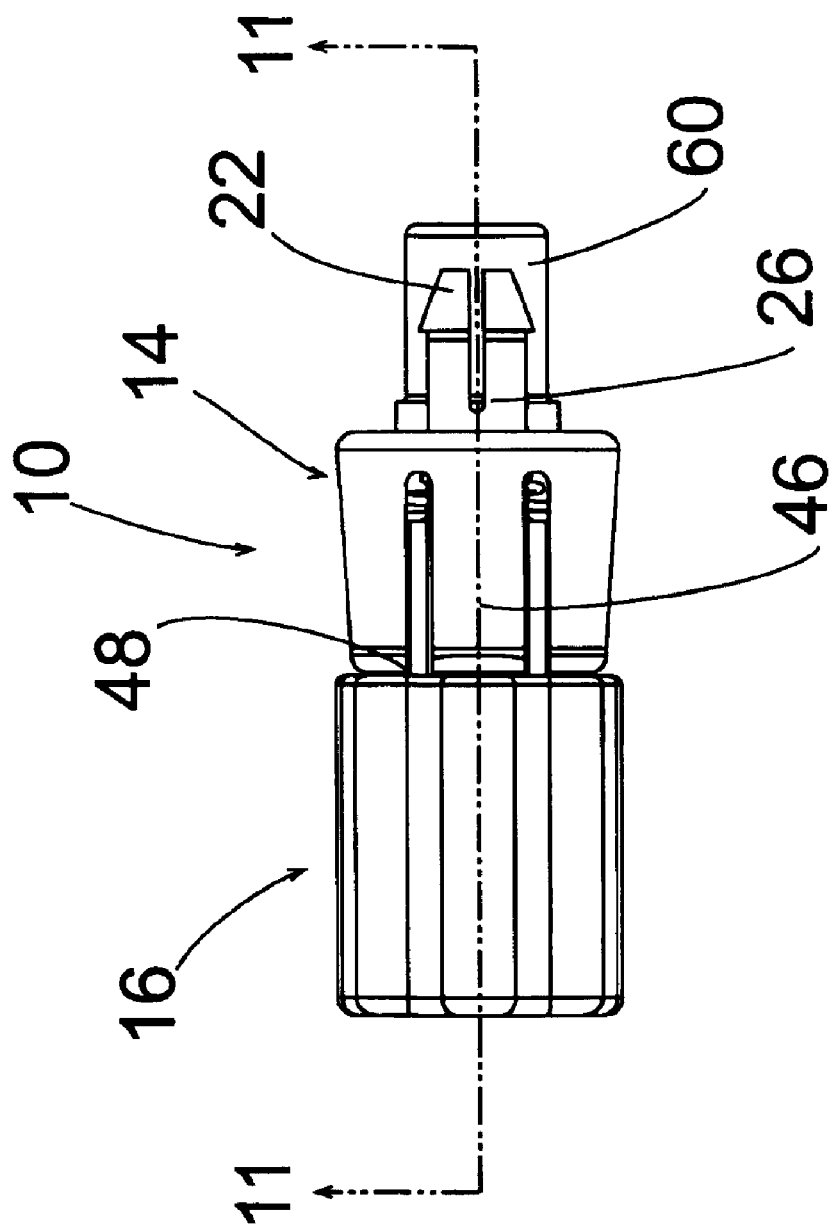
FIG. 9 is a side elevational view of the preferred embodiment of the adapter in an actuated position according to the present invention.

In operation, the adapter 10 of the present invention is uniquely configured to interconnect the fluid container 88 to the administration feeding set 90. As seen in FIG. 1, the adapter 10 is connected to the fluid container 88 by screwing the threaded portion 68 of the locking collar 16 onto the threaded portion 98 of the cap 92 while the spike 52 is isolated within the collar 16 by sliding shaft seal 18 to prevent undesirable contact and contamination of the axial spike 52. When it is desirable to actuate adapter 10 and establish fluid flow, the user will grasp spike member 14, preferably between the operator's thumb and forefinger (not shown), and urge the spike member 14 forwardly to the actuated position illustrated in FIGS. 8 and 9, through collar 16. With particular reference to FIGS. 10 and 11, the forward axial motion of spike 52 is restrained at one point by the abutment of retention edge 48 of spike member 14 with collar 16 and the spring force applied by spring 19 against spike member 14. As the spike member 14 is actuated by the user, the sliding shaft seal 18 slides along the spike 52 which is continuously and sealingly engaged therealong due to the continuous engagement between O-ring portion 125 of sliding shaft seal 18 along a portion of spike 52. Once adapter 10 has been properly actuated, the operator will simply release spike member 14 to return adapter 10 to the unactuated position, as seen in FIGS. 4a and 5. Referring back to FIGS. 10 and 11, due to the spring force applied by spring 19, the spike member 14 will be automatically biased back towards the unactuated position with spike 52 isolated within collar 16 as the sliding shaft seal 18 returns back to its original position. During this operation, sliding shaft seal 18 maintains a leak free engagement about the base 130 of spike 52.

In the preferred embodiment, body member 12, spike member 14, and locking collar 16 are constructed from a substantially rigid medical-grade material, while sliding shaft seal 18 is constructed from a substantially flexible elastic material. Most preferably, the body member 12, the spike member 14, and the locking collar 16 are constructed from a thermoplastic which is a substantially liquid impermeable material, such as ABS and the like, while sliding shaft seal 18 is constructed from a thermoplastic elastomer, thermosetting rubber or other similar elastomeric material.

It should be understood from the foregoing that, while particular embodiments of the invention have been illustrated and described, various modifications can be made thereto without departing from the spirit and scope of the present invention. Therefore, it is not intended that the invention is limited by the specification; instead, the scope of the present invention is intended to be limited only by the appended claims.

What is claimed is:

1. An adapter comprising:
    a body member having a body portion defining an annular flange and at least one leg portion extending therefrom; said body portion further including at least one protrusion formed therealong;
    a spike member coupled with said body member including a spike body defining at least one opening adapted to securely engage said at least one leg portion, said spike body further including at least one slot corresponding to said at least one protrusion, said spike member further defines a spike connected to said spike body;
    a spring, said spring disposed within said body member for applying a spring force against said spike member;
    a collar member forming a channel with opposed openings, said collar member including an annular groove adjacent one of said openings, said groove being adapted to securely engage said annular flange; and
    a hollow sliding shaft seal disposed at least partially within said body member, said sliding shaft seal including a body having opposed openings with a conduit formed therebetween, said conduit being adapted to sealingly and slidingly engage around said spike.

2. The adapter according to claim 1, wherein said sliding shaft seal further includes a sealing flange formed proximate said proximal opening and circumferentially disposed about said body portion.

3. The adapter according to claim 1, wherein said sliding shaft seal further includes a locking flange formed proximate said distal opening.

4. The adapter according to claim 1, wherein said spike is sealingly and slidingly engaged along a portion of said conduit.

5. The adapter according to claim 4, wherein said conduit sealingly and slidingly engages a base of said spike.

6. The adapter according to claim 4, wherein said conduit defines an O-ring portion that sealingly and slidingly engaged to said spike.

7. The adapter according to claim 1, wherein said conduit engages said spike during operation of the adapter and when adapter is in a free state.

8. An adapter comprising:
    a body member including a body portion having a generally cylindrical shape with an annular flange disposed on said body portion, said body member further including at least one leg portion extending from said body portion and at least one protrusion formed along said body portion;

a spike member coupled with said body member, said spike member including a spike body having at least one axial opening adapted to securely engage said at least one leg portion, said spike being reciprocable between an engaged position and a disengaged position;

a spring, said spring disposed within said body member for applying a spring force against said spike.

a collar member having a generally cylindrical shape forming a channel with opposed openings and an annular groove adjacent one of said opposed openings, said annular groove being adapted to securely engage said annular flange; and a sliding shaft seal disposed at least partially within said body member and contacting said spike such that said sliding shaft seal slidingly engages in fluid tight engagement said spike.

9. The adapter according to claim 8, wherein said sliding shaft seal is fabricated from an elastic material.

10. An adapter comprising:

a body member including a body portion and an annular flange formed around said body portion, said body member further including at least one leg portion extending from said body portion;

a spike member coupled with said body member, said spike member including a spike body having at least one axial opening adapted to securely engage said at least one leg portion, said spike member further defines a hollow spike connected to said spike body;

a spring disposed within said body member for applying a spring force against said spike;

a collar member having a generally cylindrical shape forming a channel with opposed openings, said collar member including an annular groove adjacent one of said openings to securely engage said annular flange; and a sliding shaft seal disposed at least partially within said body member, said sliding shaft seal including a body having opposed openings with a conduit defined therebetween, wherein said conduit is adapted to slidingly engage in fluid tight engagement around said spike during operation of the adapter.

11. A method for establishing a fluid conduit between a fluid container and an administration feeding set, said fluid container having a cap with an orifice, said cap including a threaded portion thereabout and a frangible membrane sealingly engaged over said orifice, said administration feeding set including tubing, the method comprising the steps of:

a) providing an adapter, said adapter including a body member slidably engageable with a spike member having a hollow spike, said spike member being slidably coupled to said body member such that said spike member is biased between an engaged position and a disengaged position by a spring, said adapter further including a sliding shaft seal defining a conduit adapted to slidingly engage in fluid tight engegement around said spike, a collar member rotatably connected to the body member, said adapter being attached to the administration feeding set;

b) engaging said threaded portion of said fluid container with said adapter;

c) driving said spike member towards the engaged position such that said foil is pierced and fluid flow communication is established between the fluid container and the administration feeding set;

d) releasing said spike member; and e) urging said spike member towards the disengaged position.

12. The method according to claim 11, wherein said step of driving further comprises:

said sliding shaft seal slidingly engaging around said spike.

13. The method according to claim 11, wherein said sliding shaft seal slidingly engages around a base of said spike.

14. The method according to claim 11, wherein said step of engaging said threaded portion to the fluid container further comprises rotating the threaded portion of locking collar onto the threaded portion of the cap.

15. The method according to claim 11, wherein said step of driving said spike member is counter biased by said spring.

16. The method according to claim 11, wherein said step of urging said spike member towards the disengaged position, further includes said spring applying a bias to said spike member.

* * * * *